US 6,602,245 B1

(12) United States Patent
Thiberg

(10) Patent No.: US 6,602,245 B1
(45) Date of Patent: Aug. 5, 2003

(54) LIGHT EMITTING MEANS FOR EXTERNAL MEDICAL TREATMENT WITH LIGHT

(75) Inventor: Rolf Thiberg, Åkersberga (SE)

(73) Assignee: Biolight Patent Holding AB, Danderyo (SE)

( * ) Notice: Subject to any disclaimer, the term of this patent is extended or adjusted under 35 U.S.C. 154(b) by 0 days.

(21) Appl. No.: 09/889,204

(22) PCT Filed: Jan. 19, 2000

(86) PCT No.: PCT/SE00/00106
§ 371 (c)(1),
(2), (4) Date: Oct. 17, 2001

(87) PCT Pub. No.: WO00/43067
PCT Pub. Date: Jul. 27, 2000

(30) Foreign Application Priority Data

Jan. 20, 1999 (SE) .............................................. 9900159

(51) Int. Cl.[7] .............................................. A61B 18/18
(52) U.S. Cl. .............................................. 606/2; 607/88
(58) Field of Search ...................... 606/2, 9, 13; 601/15, 601/18, 46, 67, 68, 69, 70, 71, 72; 607/88, 89, 90, 91, 92, 93, 94

(56) References Cited

U.S. PATENT DOCUMENTS

| | | | | |
|---|---|---|---|---|
| 5,259,380 A | * | 11/1993 | Mendes et al. ............. | 607/115 |
| 5,562,717 A | * | 10/1996 | Tippey et al. ................ | 607/41 |
| 5,616,140 A | * | 4/1997 | Prescott ...................... | 606/10 |
| 5,800,479 A | * | 9/1998 | Thiberg ....................... | 607/88 |
| 5,827,266 A | * | 10/1998 | Harel et al. .................. | 606/13 |
| 5,860,967 A | * | 1/1999 | Zavislan et al. ............. | 606/9 |
| 5,860,968 A | | 1/1999 | Wojcik et al. ............... | 606/10 |
| 6,063,108 A | * | 5/2000 | Salansky et al. ............. | 607/89 |
| 6,126,651 A | * | 10/2000 | Mayer .......................... | 606/1 |
| 6,221,095 B1 | * | 4/2001 | Van Zuylen et al. ........ | 607/88 |

FOREIGN PATENT DOCUMENTS

| | | |
|---|---|---|
| AT | 305489 | 9/1971 |
| FR | 2731357 | 9/1996 |
| SE | 502784 | 7/1995 |

* cited by examiner

Primary Examiner—Linda C. M. Dvorak
Assistant Examiner—Aaron Roane
(74) Attorney, Agent, or Firm—Alfred J. Mangels

(57) ABSTRACT

Apparatus for external medical treatment with the aid of light, including a light-emitting device to be held against or in close proximity to a patient's body. The device includes light-emitting diodes that emit monochromatic light over one or more predetermined time periods and that pulsate the emitted light in accordance with a predetermined pulse frequency or a series of pulse frequencies over the predetermined time periods. The light-emitting device includes a casing and a plate that carries the light-emitting diodes. An eccentric drive arrangement is provided and includes a first part that is fixed relative to the casing and a second part that is connected to the plate. A spring prevents rotation of the plate. An electric motor powers the eccentric drive arrangement to cause the plate carrying the light-emitting diodes to execute an oscillatory movement.

6 Claims, 2 Drawing Sheets

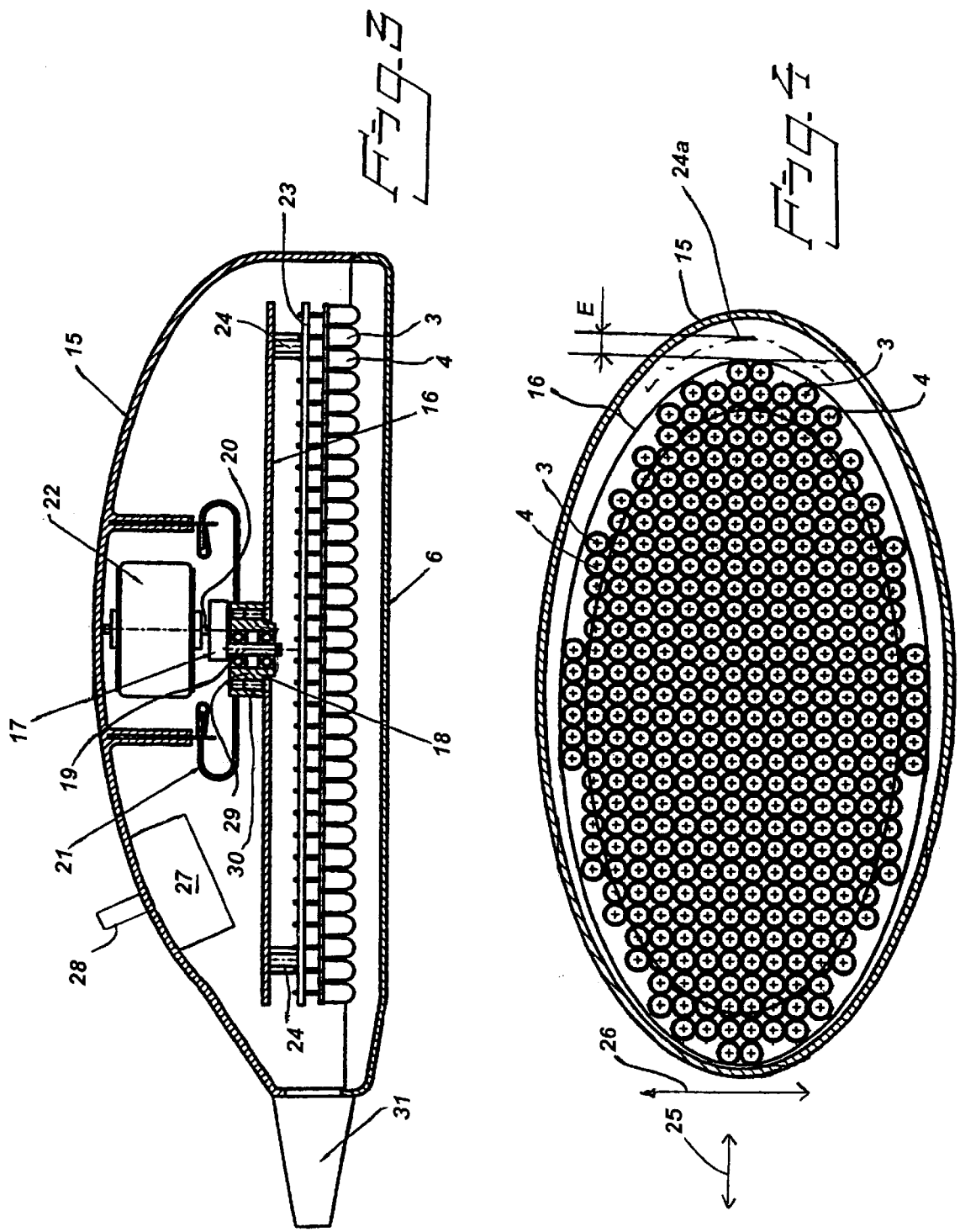

LIGHT EMITTING MEANS FOR EXTERNAL MEDICAL TREATMENT WITH LIGHT

The present invention relates to a light-emitting device for external medical treatment with the aid of light, more specifically with the aid of light which palliates and/or cures different states of diseases.

Swedish Patent Specification No. 502 784 for example teaches apparatus for external medical treatment with the aid of light that includes a light-emitting device which is intended to be held against or close to the body of an individual, and drive means for the light-emitting device, which device includes light emitting diodes or corresponding elements and is intended to emit infrared light. According to the aforesaid patent specification, the means for driving the light-emitting device is designed to control said device to emit infrared light in a first stage over a first predetermined time period and then to emit visible light in a second stage over a second predetermined time period, wherein said drive means is designed to pulsate the infrared light and the visible light in accordance with a predetermined series of pulse frequencies.

It is also known to emit other monochromatic light for treating different states of diseases.

It has also been found that very good results can be obtained when treating a patient with solely one or more monochromatic light and with light other than infrared light, such as visible light of different colours emitted in accordance with a given pulse frequency.

It has been found that a device of the aforesaid kind can be used very successfully for treating many different states of diseases and injuries, for instance sport sustained injuries, stretched muscles, muscular pain, joint pain, headaches, various inflammatory conditions, various skin complaints, such as acne, back pains, etc., provided that the light is emitted in a certain way. In this regard, treatment with light has a favourable influence on injury healing processes and will palliate and/or cure various diseases.

There is thus an understanding that treatment with certain light that is emitted in certain frequency series will have a significantly greater effect in shortening the time taken to cure or palliate a disease.

One problem with devices of this kind known hitherto is that the person administering the treatment is required to oscillate the light-emitting device whilst holding the device against or in the close proximity of that region of the patient's body to be treated. The reason for this is because the light emitting diodes disposed at the bottom of the light-emitting device have a certain geometric extension and are of different kinds, and hence two mutually adjacent light emitting diodes of mutually the same kind will be spaced at a certain distance apart. It is therefore necessary to move the light-emitting device forwards and backwards over the area to be treated, in order to ensure that the whole of said area will be irradiated uniformly to the best possible extent.

Because treatment of this kind will usually take from about two to ten minutes to carry out, administration of the treatment concerned may be very onerous to the person concerned.

This problem is solved by the invention.

Thus, the present invention relates to apparatus which is intended for external medical treatment with the aid of light and which includes a light emitting device that is intended to lie against or be held in the close proximity of the patient's body, and drive means for said device, wherein the light-emitting device includes light emitting diodes or corresponding elements which are designed to emit monochromatic light, wherein the means that drives said device is adapted to control the light-emitting device to emit one or more types of monochromatic light over one or more predetermined time periods and to pulsate said emitted light in accordance with a predetermined pulse frequency or series of pulse frequencies over said time periods, and wherein the light-emitting device includes a casing and a light-emitting-diode supporting plate, said apparatus being characterised by an eccentric element which includes a first part that is fixed in relation to said casing and a second part which is connected to said plate; and by a spring means which functions to prevent rotation of the plate; and by an electric motor which functions to drive said eccentric element such as to cause said plate carrying said light emitting diodes to perform an oscillatory movement.

The invention will now be described in more detail partly with reference to an exemplifying embodiment thereof shown on the accompanying drawings, in which FIG. 1 is a schematic block diagram of an inventive apparatus;

FIG. 3 is a cross-sectional view of a light emitting device in accordance with the invention; and FIG. 4 shows the light emitting device of FIG. 3 from beneath.

Figure 1:
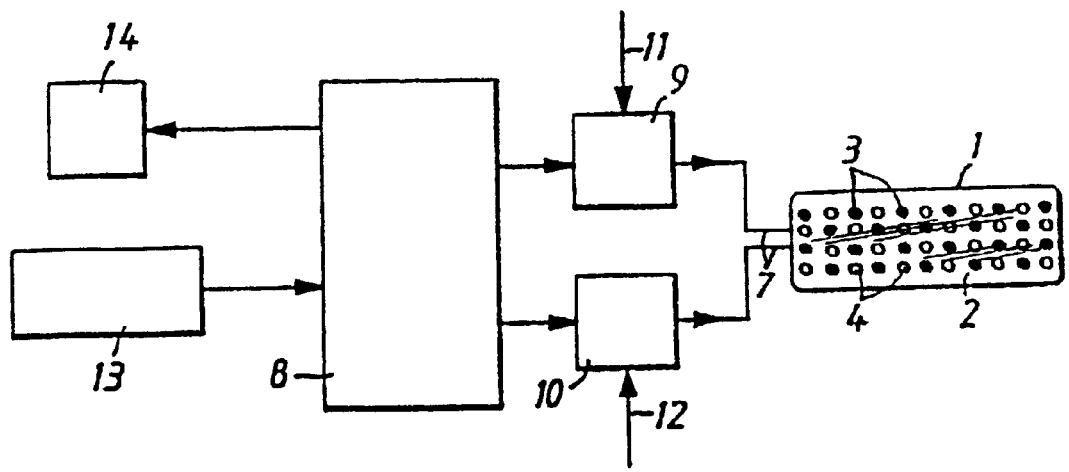
Figure 2:
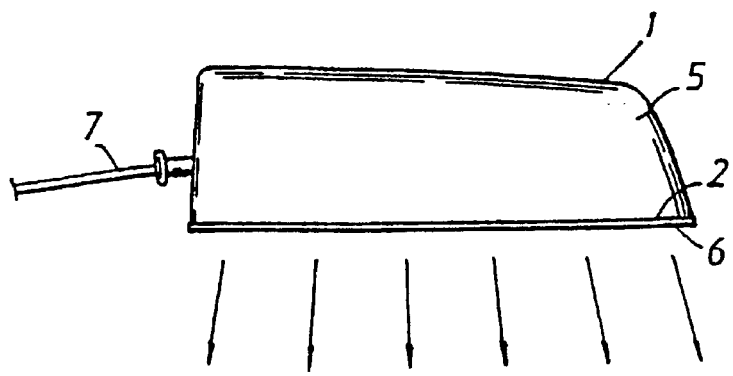
FIG. 2 is a side view of a light emitting device.

FIGS. 1 and 2 illustrate generally an apparatus for external medical treatment with the aid of light, said apparatus including a light emitting device 1 which is intended to be held against or in the close proximity of the patient's body. The light emitting device is shown from one side in FIG. 2 and from beneath in FIG. 1. This device 1 includes a casing 5 which houses a transparent plate 6. Located beneath the plate 6 is a surface 2 on which a plurality of light emitting diodes 3, 4 or corresponding elements are mounted.

The light emitting diodes thus emit light through the plate 6 when energised, i.e. when supplied with current through a cable 7.

When the device is being used, the casing 5 is held so that the plate 6 will lie against the relevant part of the patient's body.

The apparatus also includes drive means for the light emitting device 1. The drive means is adapted to control the light emitting device 1 to emit different monochromatic light on different wavelengths over different predetermined time periods, and to pulsate the light emitted in accordance with a predetermined pulse frequency or series of pulse frequencies over said time periods.

The light emitting device 1 may include light emitting diodes 3 adapted for the emission of infrared light. These diodes are shown with solid circles in FIG. 1. Visible light can be emitted with the aid of other light emitting diodes 4.

These diodes are illustrated with empty circles in FIG. 1. The infrared light diodes 3 will preferably be semiconductors of the GaAs-type (Gallium Arsenide). The diodes 4 that emit visible light will also preferably be of the GaAs-type.

The drive means includes a computer 8 which controls drive circuits 9, 10 to which signals for driving or operating the light-emitting diodes are sent from the computer via the cable 7.

The computer and the drive circuits are of a suitable known kind. The drive means or computer has connected thereto a keyboard 13 by means of which the operator can key-in data for causing the drive means to activate the light emitting device in a desired manner. The device will conveniently include a display 14 for displaying the settings entered through the keyboard. This display may be the computer screen.

The light emitting device 1 includes light emitting diodes 4 which are adapted to emit essentially monochromatic visible light in one of the colours violet, blue, yellow, orange, red or green, and also infrared light and other invisible wavelengths.

The nature of the light used will depend on the disease or the type of injury to be treated.

A large part of the above description of the drawings is also found in the aforementioned patent specification.

According to the present invention, the light emitting device 1 includes a casing 15 and a plate 16 that carries the light emitting diodes 3, 4.

There is included, in accordance with the invention, an eccentric arrangement which has a first part 17 that is fixed in relation to the casing 15, and a second part 18 that is connected to the plate 16. The first part 17 has a trunnion 19 which is offset in relation to a drive shaft 20. The second part 18 may include a bearing 29 with associated bearing casing 30, wherewith the bearing casing is fixed in the plate 16 and the trunnion 19 is inserted into the bearing.

A spring 21 prevents rotation of the plate 16. The spring will conveniently be a flat spring that is fastened in the bearing casing of said second part 18 and fixed in relation to the casing 15.

The eccentric arrangement is driven by an electric motor 22 through the medium of the drive shaft 20.

The light emitting diodes 3, 4 are illustrated in FIG. 4 by means of circles filled with a centre cross. The diodes are fastened to a carrier plate 23 which, in turn, is fastened to the plate 16 via spacer elements 24.

When the motor 22 drives the shaft 20, the plate 16 will execute an eccentric oscillatory movement instead of a rotary movement, wherewith the light emitting diodes will, of course, accompany this movement.

FIG. 4 shows the plate 16 in its farthest possible position to the left of FIG. 4. The neutral position of the plate periphery in direction 25 is shown in dash-dotted lines 24_a_ in FIG. 4. The difference in the positions between the dash-dotted line 24_a_ and the plate periphery shown in a full line in said direction 25 is equal to the eccentricity E given by the eccentric arrangement. Naturally, the plate will be displaced to a similar extent in direction 26 as the eccentric arrangement travels through a complete revolution.

According to one preferred embodiment, the eccentric arrangement has an eccentricity E of about 3 to 10 millimeters.

According to one preferred embodiment, the eccentric arrangement is driven at a speed of about 1 to 200 r.p.m. The motor 22 will conveniently be a stepping motor. The motor will also be designed for rotation in both directions.

According to another preferred embodiment, the electric motor 22 will preferably be a variable speed motor. An appropriate known control circuit 27 may be fitted to the casing 15 to this end. An outwardly projecting knob 28 may be provided for finger control of the motor speed.

The reference numeral 31 in FIG. 3 identifies a cable transit for an electric cable for powering the motor and the [light emitting] light-emitting diodes. The control circuit may be included in the drive means 8, 9, 10. In this case, the motor can be energized via said cable, therewith obviating the need for a separate control circuit 27 in the light-emitting device 1. The desired motor speed can be keyed-in through the keyboard 13.

It will be evident from the aforegoing that the present invention solves the aforesaid problem.

Although the invention has been described with reference to a number of exemplifying embodiments thereof it will be obvious that the constructive solutions for achieving oscillatory movement of the plate can be greatly varied by the man skilled in the art.

It will therefore be understood that the present invention is not restricted by the aforedescribed embodiments but that modifications and variations can be made within the scope of the accompanying Claims.

What is claimed is:

1. Apparatus for external medical treatment with the aid of light, said apparatus comprising: a light-emitting device to be held in close proximity to a patient's body, wherein said light-emitting device includes a plurality of light emitting elements that emit monochromatic light, drive means controlling the light-emitting device to emit at least one type of monochromatic light over at least one predetermined time period and to pulsate said emitted light in accordance with a predetermined pulse frequency over said at least one time period, and wherein said light-emitting device includes a casing and a plate that carries said light-emitting elements, an eccentric drive arrangement which includes a first part that is fixed relative to said casing and a second part that is connected to said plate; a spring carried by the casing to prevent rotation of the plate; and wherein the first part includes an electric motor to drive said eccentric drive arrangement so that the plate carrying said light-emitting elements executes an oscillatory movement.

2. Apparatus according to claim 1, wherein the eccentric drive arrangement provides a movement eccentricity of the plate of about 3 to 10 millimeters.

3. Apparatus according to claim 1, wherein the eccentric drive arrangement is driven at a speed of about 1 to 200 rpm.

4. Apparatus according to claim 1, wherein the electric motor is a variable-speed motor.

5. Apparatus according to claim 1, wherein the electric motor is a stepping motor.

6. Apparatus according to claim 1, wherein the light-emitting elements are light-emitting diodes.

* * * * *